(12) United States Patent
Miller et al.

(10) Patent No.: US 6,268,124 B1
(45) Date of Patent: Jul. 31, 2001

(54) NEURONAL CELL MODEL AND METHODS OF USE THEREFOR

(75) Inventors: Craig S. Miller, Nicholasville; Robert J. Danaher; Robert J. Jacob, both of Lexington, all of KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/272,158

(22) Filed: Mar. 19, 1999

Related U.S. Application Data

(60) Provisional application No. 60/078,850, filed on Mar. 20, 1998.

(51) Int. Cl.[7] .............................. C12Q 1/70; C12N 5/06
(52) U.S. Cl. ................................. 435/5; 435/6; 435/353
(58) Field of Search ........................... 435/5, 6, 353

(56) References Cited

PUBLICATIONS

Su et al., Human Corneal Cells and Other Fibroblasts Can Stimulate the Appearance of Herpes Simplex Virus from Quiescently Infected PC12 Cells. Journal of Virology 73(5):4171–4180, 1999.*

Hardwicke et al., Differential Effects of Nerve Growth Factor and Dexmethasone on Herpes Simplex Virus Type 1 oriL– and oriS–Dependent DNA Replication in PC12 Cells. Journal of Virology 71(5):3580–2587, 1997.*
Block T, et al. (1994) *J Gen Virol* 75: 2481–2487.
Greene LA (1978) *J Cell Biol* 78:747–755.
Gunning PW, et al. (1981) *J Neurosci* 1:1085–1095.
Halford WP, et al. (1996) *J Virol* 70:5051–5060.
Harris RA & Preston CM (1991) *J Gen Virol* 72:907–913.
O'Neill FJ (1977) *J Virol* 24:41–46.
O'Neill FJ, et al. (1972) *J Gen Virol* 14:189–197.
Scheck AC, et al. (1989) *Intervirology* 30:121–136.
Smith RL, et al. (1994) *Virology* 202:49–60.
Wigdahl BL, et al. (1982a) *Virology* 116:468–479.
Wigdahl BL, et al. (1982b) *Science* 217:1145–1146.
Wigdahl BL, et al. (1983) *Virology* 127:159–167.
Wilcox CL & Johnson Jr EM (1987) *J Virol* 61:2311–2315.
Wilcox CL & Johnson Jr EM (1988) *J Virol* 62:393–399.

* cited by examiner

*Primary Examiner*—Donna C. Wortman
(74) *Attorney, Agent, or Firm*—McDermott, Will & Emery

(57) ABSTRACT

The present invention provides, inter alia, a PC12 cell quiescently infected with a neurotropic virus. Preferred quiescently-infected neural cells are those wherein the neurotropic virus is a neurotropic herpes virus. Methods related to these and other materials are also provided.

17 Claims, 4 Drawing Sheets

NEURONAL CELL MODEL AND METHODS OF USE THEREFOR

This application claims priority to U.S. Provisional Patent Application No. 60/078,850, filed Mar. 20, 1998.

This work was supported by NIH grant number NIH (NIDR) R29 DE11104; the government may have certain rights in this invention.

FIELD OF THE INVENTION

In this disclosure, it is demonstrated that neurally-differentiated cells can be infected with viruses in a manner that supports a long-term non-productive infection. This model when compared to others is unique in that 1) quiescent infection is established in a neuronal cell line that has features reminiscent of ganglionic neurons, 2) an inhibitor of DNA synthesis is needed only to establish the quiescent state, not maintain it, 3) an inhibitor of viral gene expression is not required to establish the quiescent state, 4) the non-productive state is reversible with spontaneous and inducible reactivation, and 5) quiescence is long term.

In particular, neuronally differentiated PC12 cells, established from pheochromocytoma of rat adrenal medulla, are used to host a persistent viral infection. First, cells are differentiated by growing cells in defined medium containing nerve growth factor. Under these conditions cells extend neurites, develop electrical excitability and express genes encoding neuronal cell-specific proteins (Green and Tischler 1976; Green and Tischler 1982). Cells are maintained in serum-free medium to render them nondividing. Next, cells are inoculated with neurotropic virus (eg., human herpes virus) under conditions that restrict viral propagation. A defined regimen of media changes are used to establish a quiescent and nonproductive state following the withdrawal of the antiviral treatment. Evidence of establishment of a quiescent and persistent infection comes from assays demonstrating that cells survive the infection, a nonproductive viral state is established in the majority of cultures, and cells support spontaneous and inducible virus production.

BACKGROUND OF THE INVENTION

The lack of a universally accepted neural cell-line that supports viral latency, in particular, HSV-1 latency, has restricted the understanding of the molecular events involved in reactivation from latency. As a result, animals and tissue culture have served to provide an understanding of the mechanisms of this event. Animal models, however, are limited by difficulties. These include: (i) latency and reactivation events that are influenced by viral strains with different primary growth phenotypes, (ii) the limited number of neurons latently infected in animal models (Bloom et al, 1996; Hill et al, 1996; Maggioncalda et al, 1996; Mehta et al, 1995; Ramakrishnan 1994; Sawtell, 1997; Sawtell et al, 1998; Thompson and Sawtell, 1997), and (iii) inaccurate quantitation of reactivation events when measuring virus production at the recurrent site as a result of influences of transport, replication in epithelium, and the immune response.

A major advantage of tissue and cell culture models includes the ability to observe virus at the single cell level without the overlay of immunological events that modulate the eventual appearance of virus in the host. Tissue culture models derived from neuronal and sympathetic ganglia have properties of the in vivo system including: (i) restricted transcription of the HSV genome (Doerig et al, 1991; Halford et al, 1996; Smith et al, 1992; Smith et al, 1994), (ii) lack of virus production following removal of the inhibitory agent, (Wilcox and Johnson, 1988) (iii) the presence of latency-associated transcripts (LATs) (Doerig et al, 1991; Smith et al, 1994), (iv) impaired reactivation of thymidine kinase negative virus (Wilcox et al, 1992), and (v) inducible reactivation (Halford et al, 1996; Moriya et al, 1994; Smith et al, 1992; Wilcox and Johnson, 1988; Wilcox and Johnson 1987; Wilcox et al, 1990). Nevertheless, preparation of dissected ganglia is inconvenient, material is limited, animal use is required, and axotomy introduces traumatic factors that influence reactivation of virus.

For the above reasons, cell culture models are important for studying the molecular details of the establishment, maintenance and reactivation stages of latency. Cell culture also allows for an unlimited supply of a defined host cell and the ability to manipulate genetic material. Over the past 25 years, cell culture systems using fibroblast cultures (Harris and Preston, 1991; Jamieson et al, 1995; O'Neill, 1977; O'Neill et al, 1972; Russell et al, 1987; Scheck et al, 1989; Wigdahl et al, 1982a; Wigdahl et al, 1982b; Wigdahl et al, 1983) and lymphocytes (Hammer et al, 1981; Youssoufian et al, 1982) have enabled the study of HSV-1 during a latent-like state.

These models, however required low input multiplicities and/or the use of replication inhibitors such as anti-viral agents, inhibitory temperatures, or the use of a mutant virus, to prevent virus production. A cell line that has neural morphology and physiology, can survive infection and permit viral production, allow establishment of a long term nonproductive viral infection, and support virus in a state suitable for reactivation studies would be more desirable.

The rat pheochromocytoma (PC12) cell line (used in the present model) is of neural crest origin and can be morphologically differentiated with the addition of nerve growth factor (Greene and Tischler, 1976). These cells have been shown to be permissive to HSV-1 infection (Bloom and Stevens, 1994; Rodahl and Haar, 1997; Rubenstein and Price, 1983a; Rubenstein and Price 1983b, Rubenstein and Price, 1984), and have been used to examine HSV-1 gene regulation and expression (Frazier et al, 1996a; Frazier et al, 1996b; Jordan et al, 1998; Leib et al, 1991; Xie et al, 1996) and the function of HSV origins of DNA replication (Hardwicke and Schaffer, 1997). The relevance of these studies, however remains incomplete since the ability of these cells to harbor HSV-1 in a "latent-like" state has not been demonstrated (Block et al, 1994). Block also differs from the present invention in that Block asserted that withdrawal of NGF from a serum-containing medium resulted in reactivation, implying that NGF and serum were necessary in any such model.

Previous studies have demonstrated NGF-differentiated PC12 (Nd-PC12) cells can be maintained as non-dividing cultures both in the presence and absence of serum (Greene, 1978; Greene and Tischler, 1976). These cultures have been studied on non-coated (Block et al, 1994) and collagen coated dishes (Greene and Tischler, 1976). Other studies indicate that a significant portion of PC12 cells cultured in the presence of serum continue to divide (Goodman et al, 1979; Ignatius et al, 1985).

References Cited in this Application

Bloom, D C, et al. (1994)*J Virol* 68:3761–3772.
Bloom, D C, et al. (1996)*J Virol* 70:2449–2459.
Block T., et al. (1994)*J Gen Virol* 75: 2481–2487.
Brown T (1993)*Current Protocols in Molecular Biology.* Greene Publishing Associates, Inc. and John Wiley & Sons, Inc.
Devi-Rao G B, et al. (1994)*J Virol* 68:1271–1282.

Doerig C, et al. (1991)*Virology* 183:423–426.
Frazier D P, et al. (1996)*J Virol* 70:7433–7444.
Frazier D P, et al. (1996)*J Virol* 70:7424–7432.
Goodman R, et al. (1979)*Cold Spring Harbor Conf Cell Proliferation* 6:653–669.
Greene L A (1978)*J Cell Biol* 78:747–755.
Greene L A & Tischler A S (1976)*Proc Natl Acad Sci USA* 73:2424–2428.
Gunning P W, et al. (1981)*J Neurosci* 1:1085–1095.
Halford W P, et al. (1996)*J Virol* 70:5051–5060.
Hammer S M, et al. (1981)*J Immunol* 127:144–148.
Hardwicke M A & Schaffer P A (1997)*J Virol* 71:3580–3587.
Harris R A & Preston C M (1991)*J Gen Virol* 72:907–913.
Hill J M, et al. (1996)*J Virol* 70:3137–3141.
Huang R D, et al. (1982)*J Cyclic Nucleotide Res* 8:385–94.
Ignatius M J, et al. (1985)*J Neurosci* 5:343–351.
Ikeda Y, et al. (1996)*Virus Res* 41:201–207.
Jamieson D R S, et al. (1995)*J Gen Virol* 76:1417–1431.
Jordan R, et al. (1998)*J Virol* 72:5373–5382.
Kosz-Vnenchak M, et al. (1993)*J Virol* 67:5383–5393.
Leib D A, et al. (1991)*Proc Natl Acad Sci USA* 88:48–52.
Lynas C, et al. (1989)*J Gen Virol* 70:2345–2355.
Maggioncalda J, et al. (1996)*Virology* 225:72–81.
McGeoch D J, et al. (1988)*J Gen Virol* 69:1531–1574.
McGeoch D J, et al. (1986)*Nucleic Acids Res* 14:1727–1745.
Mehta A, et al. (1995)*Virology* 206:633–640.
Miller C S & Smith K O (1991)*J Dent Res* 70:111–117.
Moriya A, et al. (1994)*Arch Virol* 135:419–425.
Nichol P F, et al. (1996)*J Virol* 70:5476–5486.
O'Neill F J (1977)*J Virol* 24:41–46.
O'Neill F J, et al. (1972)*J Gen Virol* 14:189–197.
Park T-J & Kim K-T (1996)*J Neurochem* 66:83–88.
Perry L S & McGeoch D J (1988)*J Gen Virol* 69:2831–2846.
Ramakrishnan R, et al. (1994)*J Virol* 68:1864–1873.
Rodahl E & Haarr L (1997)*J Virol* 71:1703–1707.
Rubenstein R & Price R W (1983a)*J Gen Virol* 64:2505–2509.
Rubenstein R & Price R W (1983b)*Arch Virol* 78:49–64.
Rubenstein R & Price R W (1984)*J Neurochem* 42:142–150.
Russell J, et al. (1987)*J Gen Virol* 68:3009–3018.
Sawtell N M (1997)*J Virol* 71:5423–5431.
Sawtell N M, et al. (1998)*J Virol* 72:5343–5350.
Scheck A C, et al. (1989)*Intervirology* 30:121–136.
Seamon K B & Daly J W (1981)*J Biol Chem* 256:9799–9801.
Seamon K B & Daly J W (1986)*Adv Cyclic Nucleotide Res* 20:1–150.
Smith R L, et al. (1994)*Virology* 202:49–60.
Smith R L, et al. (1992)*Virology* 188:311–318.
Thompson R L & Sawtell N M (1997)*J Virol* 71:5432–5440.
Wigdahl B L, et al. (1982a)*Virology* 116:468–479.
Wigdahl B L, et al.(1982b)*Science* 217:1145–1146.
Wigdahl B L, et al. (1983)*Virology* 127:159–167.
Wilcox C L & Johnson Jr E M (1987)*J Virol* 61:2311–2315.
Wilcox C L & Johnson Jr E M (1988)*J Virol* 62:393–399.
Wilcox C L, et al. (1990)*J Neurosci* 10:1268–1275.
Wilcox C L, et al. (1992)*Virology* 187:348–352.
Xie K, et al. (1996)*J Virol* 70:1050–1060.
Youssoufian H, et al. (1982)*Proc Natl Acad Sci USA* 79:2207–2210.

Citation of the above documents is not intended as an admission that any of the foregoing is pertinent prior art. All statements as to the date or representation as to the contents of these documents is based on subjective characterization of information available to the applicant, and does not constitute any admission as to the accuracy of the dates or contents of these documents.

SUMMARY OF THE INVENTION

The present invention provides, inter alia, neural cells comprising a PC12 cell quiescently infected with a neurotropic virus. Preferred quiescently-infected neural cells are those wherein the neurotropic virus is a neurotropic herpes virus. More preferred are quiescently-infected neural cells wherein the neurotropic virus is a neurotropic human herpes virus. More preferred are quiescently-infected neural cells wherein the neurotropic herpes virus is a human herpes simplex 1 virus. However, those quiescently-infected neural cells wherein the neurotropic virus is selected from the group consisting essentially of varicella zoster viruses, polyoma viruses, measles viruses, human immunodeficiency viruses, papillomaviruses, adenoviruses, cytomegaloviruses, epstein barr viruses, hepatitis viruses, coronaviruses, coxsackie viruses, rabies viruses, flaviviruses, paramyxoviruses, togaviruses, and rhinoviruses, are also preferred.

Also provided are methods of establishing quiescently-infected neural cells, comprising introducing a neurotropic virus to neurally-differentiated and viable PC12 cells in a serum-free medium, said differentiated PC12 cells being in a container; and incubating said container with an antiviral reagent for a time necessary to accomplish quiescence of viral activity; and removing said antiviral agent from said container. Preferred such methods are those wherein the neurotropic virus is a neurotropic herpes virus. More preferred are those methods wherein the neurotropic herpes virus is a human herpes simplex 1 virus. However, those methods wherein the neurotropic virus is selected from the group consisting essentially of varicella zoster viruses, polyoma viruses, measles viruses, human immunodeficiency viruses, papillomaviruses, adenoviruses, cytomegaloviruses, epstein barr viruses, hepatitis viruses, coronaviruses, coxsackie viruses, rabies viruses, flaviviruses, paramyxoviruses, togaviruses, and rhinoviruses are also preferred. Methods wherein the neurotropic herpes virus is a human herpes simplex 1 virus and the antiviral agent is acyclovir are preferred, especially methods wherein said container is incubated with an antiviral composition for approximately 5 to 12 days, more especially methods wherein said container is incubated at a temperature less than 40 degrees Celsius, and most especially wherein said serum free medium allows for constant cell density and imparts neural characteristics to said cells.

Also provided are methods of reactivating a quiescent virus from neural cell, comprising: introducing a reactivator to a quiescendy-infected neural cell described herein.

Also provided are methods for determining the ability of a test reagent to suppress virus reactivation from a quiescently-infected neural cell, comprising introducing a test reagent to a quiescently-infected neural cell described herein; and introducing to said neural cell a reactivator; and determining if reactivation has been suppressed.

Also provided are methods for determining the ability of a test reagent to induce virus reactivation from in a neural cell, comprising introducing a test reagent to a quiescently-infected neural cell described herein; and determining if reactivation has been induced.

Also provided are methods for eliciting phenotypic change in a neural cell, introducing a reactivator to a quiescently-infected neural cell described herein, and eliciting a phenotypic change in said neural cell. Preferred are such methods wherein said phenotypic change is selected from the group consisting of synthesis of myelin, synthesis of neurotransmitter, cell death, and viral shedding.

Also provided are methods for determining the susceptibility of a person infected with a quiescent virus to reactivation by a reagent, comprising introducing a reactivator to a quiescently-infected neural cell described herein, wherein the neurotropic virus is a strain isolated from a person infected with said neurotropic virus; and determining the relative magnitude of phenotypic or genomic reactivation.

Also provided are methods to determine the ability of a non-neurotropic virus to become quiescent and/or reactivatable in a neural cell line, comprising introducing a non-neurotropic virus to differentiated and viable PC12 cells in a serum-free medium, said differentiated PC12 cells being in a container; and incubating said container with an antiviral reagent for a time necessary to accomplish quiescence of viral activity; and removing said antiviral agent from said container; and determining said non-neurotropic virus's ability to become quiescent and or reactivatable.

Also provided are methods to identify nucleic acid molecules and/or proteins involved in virus reactivation, comprising reactivating a quiescently-infected neural cell described herein with a reactivator; and identifying nucleic acid molecules and/or proteins which are uniquely expressed during reactivation.

Also provided are methods to identify the origins of DNA replication important to virus reactivation, comprising reactivating a quiescently-infected neural cell described herein with a reactivator; and identifying the origins of replication which are uniquely associated with reactivation.

Also provided are methods to determine a reagent's ability to inhibit establishment of a quiescent viral infection, comprising introducing a non-neurotropic virus to differentiated and viable PC12 cells in a serum-free, test reagent-containing medium, said differentiated PC12 cells being in a container; and incubating said container with an antiviral reagent for a time necessary to accomplish quiescence of viral activity in the absence of said test reagent; and removing said antiviral agent from said container; and determining said test reagent's ability to inhibit quiescence.

Also provided are methods to screen an attenuated virus' relative ability to be reactivated, comprising introducing a reactivator to a quiescently-infected neural cell described herein, wherein the neurotropic virus is an attenuated virus; and determining the relative magnitude of reactivation.

For the purposes of the present application, the following terms shall have the following meanings:

"a" or "an", when describing a noun, refers to one or more of that noun.

"antiviral reagent" means a reagent which prevents viral growth or DNA replication in a cell.

"composition" means any compound or composition made by any means. "Composition" includes synthetic or naturally-occurring compounds or compositions, whether purified or not, and can include: biologicals, chemicals, herbal extract(s); precursor(s); metabolite(s); and ingredient(s), including enantiomer(s) of a racemic mixture. The definition of "composition" includes compounds produced in situ by virtue of an immune response (ie. immunoglobulins and compounds involved in inflammation), as well as organisms, such as: viruses, bacteria and fungi.

"isolated" means physically removed from a form found in nature. For instance, whole cells, a crude cell extract, purified virus, molecularly engineered virus, or artificial virus would be "isolated" virus.

"neurotropic virus" means any virus which is capable of infecting neurons, including viruses which only transiently infect neurons.

"quiescent" or "quiescence" means the absence of detectable infectious particles in the media and within the cells, no detectable gene products, no detectable viral gene transcription, except for latency associated transcripts.

"reactivator" means a reagent which will cause reactivation of quiescent virus.

"reactivation" means any change in phenotype or genotype from a quiescent state.

"reagent" means a composition or an environmental condition, temperature, ultraviolet radiation, etc.

"virus" means the definition as understood by those in the art, as well as viroid particles such as prions, and including natural and artificial alterations thereof (eg. mutations (eg. temperature sensitive mutations), including deletions, insertions, etc.)

DETAILED DESCRIPTION OF THE INVENTION

Figure 1:
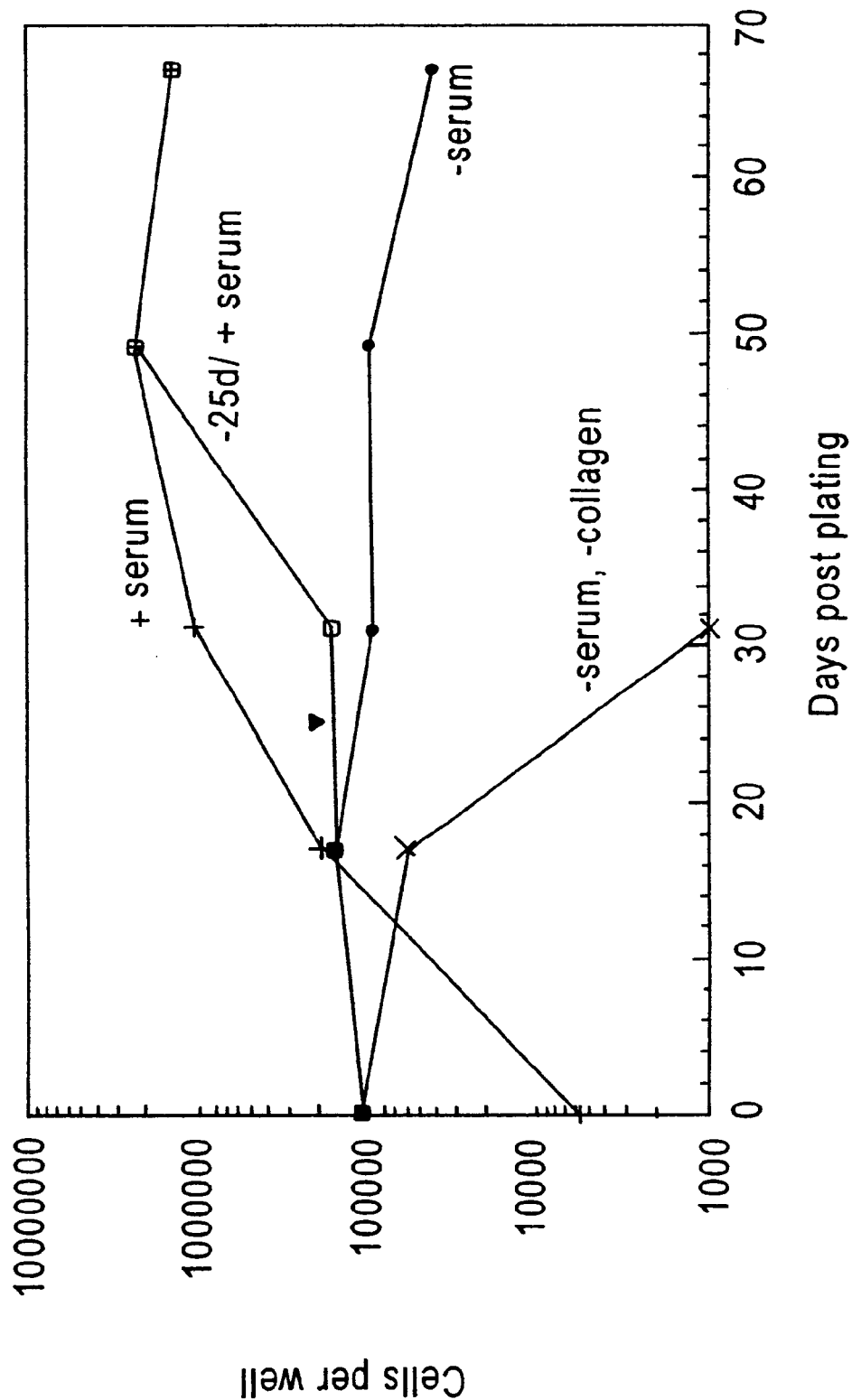
FIG. 1 shows the growth characteristics of long-term cultures of NGF differentiated PC12 cells.

The present invention provides, inter alia, neural cells comprising a PC12 cell quiescently infected with a neurotropic virus. Preferred quiescently-infected neural cells are those wherein the neurotropic virus is a neurotropic herpes virus. More preferred are quiescently-infected neural cells wherein the neurotropic virus is a neurotropic human herpes virus. More preferred are quiescently-infected neural cells wherein the neurotropic herpes virus is a human herpes simplex 1 virus. However, those quiescently-infected neural cells wherein the neurotropic virus is selected from the group consisting essentially of varicella zoster viruses, polyoma viruses, measles viruses, human immunodeficiency viruses, papillomaviruses, adenoviruses, cytomegaloviruses, epstein barr viruses, hepatitis viruses, coronaviruses, coxsackie viruses, rabies viruses, flaviviruses, paramyxoviruses, togaviruses, and rhinoviruses, are also preferred.

Certain PC12 cells are available commercially as described in the examples. PC12 cell variants are within the scope of the present invention, as are any cells derived from the neural crest. These materials can be commercially obtained from American Type Culture Collection (ATCC, Rockville, Md.) or other commercial entities. These cells are within the scope of the present invention as well.

Within the meaning of each of the viruses listed in the claims are several hundreds of "strains" of those viruses. For instance, human herpes virus 1, human herpes virus 6, human herpes virus 7, and human herpes viruses 8 are "strains" of human herpes virus. The strains of each virus type is, of course, included within the scope of the present invention. For instance, human herpes simplex virus 1 includes the strains listed in the examples, as well as these other strains, such as 17+, KOS, McKrae, Macroplaque, Patton, and F.

Viruses can be obtained by purchasing them commercially (as part of a cell line or tissue sample) from ATCC or by obtaining them according to the procedures well known in the art, such as by obtaining clinical isolates, or cultures from researches in the field. Textbooks which discuss manipulations of viruses are many, including: Fields & Knipe, Fundamental Virology; Luria et al, General Virology; and Fenner et al., Molecular Virology. The present quiescently-infected neural cells can be made by the methods disclosed herein.

Particularly useful in the preparation of the neural cells are the examples, although variations as described herein will also produce the present materials. Moreover, certain reasonable optimization of the methods can be accomplished according to methods well-known in the art.

Also provided are methods of establishing quiescently-infected neural cells, comprising introducing a neurotropic virus to neurally-differentiated and viable PC12 cells in a serum-free medium, said differentiated PC12 cells being in a container; and incubating said container with an antiviral reagent for a time necessary to accomplish quiescence of viral activity; and removing said antiviral agent from said container. Preferred such methods are those wherein the neurotropic virus is a neurotropic herpes virus. More preferred are those methods wherein the neurotropic herpes virus is a human herpes simplex 1 virus. However, those methods wherein the neurotropic virus is selected from the group consisting essentially of varicella zoster viruses, polyoma viruses, measles viruses, human immunodeficiency viruses, papillomaviruses, adenoviruses, cytomegaloviruses, epstein barr viruses, hepatitis viruses, coronaviruses, coxsackie viruses, rabies viruses, flaviviruses, paramyxoviruses, togaviruses, and rhinoviruses are also preferred. Methods wherein the neurotropic herpes virus is a human herpes simplex 1 virus and the antiviral agent is acyclovir are preferred, especially methods wherein said container is incubated with an antiviral composition for approximately 5 to 12 days, more especially methods wherein said container is incubated at a temperature less than 40 degrees Celsius, and most especially wherein said serum free medium allows for constant cell density and imparts neural characteristics to said cells.

The methods described herein may utilize the specific conditions described in the examples, but may also vary therefrom. Variations include the use of collagen in the plating technique; collagen need not be used, but efficiency will be improved if it is. Moreover, the plates need not be as confining as described in the examples; other surfaces, including different shapes and sizes, can be used, so long as a viable cell culture can be maintained for the length of time desired. The multiplicity of infection may be from 0.5 to greater than 15, although it the examples describe preferred multiplicities for HSV-1 when high reactivation rates are desired. However, in certain instances, it may be optimal to have low reactivation rates, depending on the particular use of the neural cells. In that case, lower multiplicities would be optimal. The antiviral reagent used can be any which causes quiescence of the neurotrophic virus. The exemplified reagent, acyclovir, may be optimized chemically for this purpose, or other antivirals may be used. For example, AZT, lamidudine (3TC) indovir (IDV), gancyclovir, fancyclovir, foscamite, idoxyuridine, phosphoacetic acid, 5-fluorouracil, or similar compounds and analogs thereof may be used. The concentrations of the compound used to cause quiescence can also be modified as necessary. Moreover, a combination (eg. two or more) of antiviral drugs may be used. Incubation of the PC12 cells with the antiviral is optimally that described in the examples, but can be more or less, depending on the particular reagent used. Optimization of the incubation schedule is within the skill of the art. Lastly, the media used can be any that allows viable cell growth, so long as it allows for constant cell density and may be supplemented reagent or virus in order to transiently inhibits viral growth. It is optimal to change the media as described in the examples, but it is not necessary, so long as the cells are acceptably viable.

Also provided are methods of reactivating a quiescent virus from neural cell, comprising: introducing a reactivator to a quiescently-infected neural cell described herein.

This aspect of the invention is particularly useful in studying reactivation, as well as in studying quiescence. The information gleaned from reactivation and quiescence studies will be of benefit in drug discovery. The preferred quiescently-infected neural cells for use in this embodiment are those comprising neurotropic herpes viruses, preferably HSV-1. The neural cells can be prepared as described herein and introducing a reactivator can be accomplished according by any means which causes reactivation.

Also provided are methods for determining the ability of a test reagent to suppress virus reactivation from a quiescently-infected neural cell, comprising introducing a test reagent to a quiescently-infected neural cell described herein; and introducing to said neural cell a reactivator; and determining if reactivation has been suppressed.

This aspect of the invention is particularly useful for identifying potential anti-viral drugs. The preferred quiescently-infected neural cells for use in this embodiment are those comprising neurotropic herpes viruses, preferably HSV-1. The neural cells can be prepared as described herein, introducing a reactivator can be accomplished by any means which causes reactivation, and determining reactivation can be accomplished by any means, including, for example, those means described in the examples, or other well-known means.

Also provided are methods for determining the ability of a test reagent to induce virus reactivation from a neural cell, comprising introducing a test reagent to a quiescently-infected neural cell described herein; and determining if reactivation has been induced.

This aspect of the invention is particularly useful for identifying potential reactivators. In one aspect, this embodiment is useful in drug discovery as part of a toxicology screen. For example, if a reagent such as a drug (or potential drug), vaccine, carrier, food, or environmental condition is implicated through the use of this method as a reactivator of quiescent virus, it would be advisable for an infected individual to avoid the reagent, since reactivation of virus is normally a detrimental to the individual. The preferred quiescently-infected neural cells for use in this embodiment are those comprising neurotropic herpes viruses, preferably HSV-1. The neural cells can be prepared as described herein, introducing a test compound can be accomplished by any means which causes interaction between the test compound and the neural cells, and determining reactivation can be accomplished by any means, including, for example, those means described in the examples, or other well-known means.

Also provided are methods for eliciting phenotypic change in a neural cell, introducing a reactivator to a quiescently-infected neural cell described herein, and eliciting a phenotypic change in said neural cell. Preferred are such methods wherein said phenotypic change is selected from the group consisting of synthesis of myelin, synthesis of neurotransmitter, degradation of neurotransmitters, cell death, and viral shedding.

This aspect of the invention is particularly useful in studying disease states, such as multiple sclerosis, or other neuron-associated diseases. The neural cells can be directed via molecular techniques, for example, to result in disease state upon activation. Alternatively, the neural cells can be directed to be positive influences on the environment, such that gene therapy studies will be possible using this embodiment. In all aspects of the present embodiment, the methods will be useful for drug discovery in that the mechanisms of phenotypic change can be studied. The preferred quiescently-infected neural cells for use in this embodiment are those comprising neurotropic herpes viruses, preferably HSV-1.

Also provided are methods for determining the susceptibility of a person infected with a quiescent virus to reactivation by a reagent, comprising introducing a reactivator to a quiescently-infected neural cell described herein, wherein the neurotropic virus is a strain isolated from a person infected with said neurotropic virus; and determining the relative magnitude of phenotypic or genomic reactivation.

This aspect of the present invention is particularly useful for patient diagnosis and directed medical care. Since some strains are more reactivatable than others, it is important to determine the aggressiveness and/or timing of treatment. The present embodiment, for example, can identify those individuals who harbor a strain particularly reactivatable by sunlight, in which those patients could use sunscreen or avoid the sun. The method would provide information to patients who have a less reactivatable strain, so that suppressor drug levels can be lowered in comparison to those who have a highly reactivatable strain. The preferred quiescently-infected neural cells for use in this embodiment are those comprising neurotropic herpes viruses, preferably HSV-1.

Also provided are methods to determine the ability of a non-neurotropic virus to become quiescent and/or reactivatable in a neural cell line, comprising introducing a non-neurotropic virus to differentiated and viable PC12 cells in a serum-free medium, said differentiated PC12 cells being in a container; and incubating said container with an antiviral reagent for a time necessary to accomplish quiescence of viral activity; and removing said antiviral agent from said container; and determining said non-neurotropic virus's ability to become quiescent and or reactivatable.

This aspect of the present invention is particularly useful to identify additional viruses which may be amenable to the present invention. The preferred quiescently-infected neural cells for use in this embodiment are those comprising neurotropic herpes viruses, preferably HSV-1.

Also provided are methods to identify nucleic acid molecules and/or proteins involved in virus reactivation, comprising reactivating a quiescently-infected neural cell described herein with a reactivator; and identifying nucleic acid molecules and/or proteins which are uniquely expressed during reactivation.

This aspect of the present invention is particularly useful for general scientific research or to study possible targets for drug discovery. The preferred quiescently-infected neural cells for use in this embodiment are those comprising neurotropic herpes viruses, preferably HSV-1.

Also provided are methods to identify the origins of DNA replication important to virus reactivation, comprising reactivating a quiescently-infected neural cell described herein with a reactivator; and identifying the origins of replication which are uniquely associated with reactivation.

This aspect of the present invention is particularly useful for general scientific research or to study possible targets for drug discovery. The preferred quiescently-infected neural cells for use in this embodiment are those comprising neurotropic herpes viruses, preferably HSV-1.

Also provided are methods to determine a reagent's ability to inhibit establishment of a viral infection, comprising introducing a non-neurotropic virus to differentiated and viable PC12 cells in a serum-free, test reagent-containing medium, said differentiated PC12 cells being in a container; and incubating said container with an antiviral reagent for a time necessary to accomplish quiescence of viral activity in the absence of said test reagent; and removing said antiviral agent from said container; and determining said test reagent's ability to inhibit quiescence.

This aspect of the invention is particularly useful for identifying reagents which could be used as an anti-viral drug. The reagents identified as inhibiting the establishment of quiescence would be particularly effective to administer during the first lytic phase of a viral infection. The preferred neural cells for use in this embodiment are those which are neurotropic herpes viruses, specifically HSV-1.

Also provided are methods to screen an attenuated virus' relative ability to be reactivated, comprising introducing a reactivator to a quiescently-infected neural cell described herein, wherein the neurotropic virus is an attenuated virus; and determining the relative magnitude of reactivation.

This aspect of the invention is particularly useful to determine the reactivatability of potential or actual vaccines. Vaccines which can reactivate, whether alone, or in combination with an additional reagent, would be potentially dangerous. In other words, this aspect of the invention can be used a specially-designed toxicology assay. The preferred quiescently-infected neural cells for use in this embodiment are those comprising neurotropic herpes viruses, preferably HSV-1.

EXAMPLES

Example 1

Media, Cell Lines and Virus

Rat pheochromocytoma (PC12) and Vero (African green monkey kidney) cells were obtained from ATCC (Rockville, Md.). All culture media and supplements were purchased from Gibco BRL (Gaithersburg, Md.) unless otherwise indicated. PC12 cells were grown in RPMI 1640 media containing 5% fetal bovine serum (FBS) and 10% heat-inactivated horse serum (HS). Vero cells were grown and maintained in M199 medium containing 5% FBS. Cells were incubated at 37° C. in a humidified incubator with 5% CO2. All media was supplemented with penicillin (100 units/ml) and streptomycin (100 mg/ml). HSV-1 KOS (M) was a kind gift of R. Thompson (University of Cincinnati, Cincinnati, Ohio). HSV-1 strain 17 was a kind gift of N. Fraser (Wistar Institute, Philadelphia, Pa.). Viral stocks were prepared in Vero cells and maintained at −85° C. Virus production was determined using supernatants from infected cultures in a direct plaque assay (DPA) on monolayers of Vero cells as previously described (Miller and Smith, 1991).

Example 2

Morphologic Differentiation

PC12 cells were collected from flasks, dissociated by passage through a 22-gauge needle and plated on 6-or 12-well tissue culture dishes (Becton Dickinson Labware, Franklin Lakes, N.J.) coated with rat tail collagen type 1 (Becton Dickinson), unless otherwise indicated. Collagen was applied as recommended by the supplier. Morphologic differentiation was initiated with 50 ng/ml of 2.5 S mouse nerve growth factor (NGF) (Becton Dickinson) in RPMI1640 media containing 5% FBS and 10% HS or RPMI containing 0.1% bovine serum albumin, fraction V (BSA) as described by Green and Tischler (1976), Green (1978) and Gunning et al (1981). Morphologic differentiation was confirmed by microscopic visualization of dendritic processes. Media was changed every 2–3 days.

Example 3
Establishment of a Quiescent and Persistent Infection

Neurally-differentiated PC12 cells (Nd-PC12) were infected with virus, in a volume of 0.4 or 1.0 ml/well, for 12- and 6-well plates, respectively, without agitation at the indicated multiplicity of infection (MOI) overnight at 37° C. Acycloguanosine (ACV), purchased from Sigma (St. Louis, Mo.) was added to the medium, at the indicated concentrations, from days −1 to the indicated time post-infection (p.i.). After ACV withdrawal, a quiescent state (i.e., free of detectable infectious virus in culture supernatants and lysates) was maintained for at least 7 days prior to induction.

Example 4
Reactivation Stimuli

HSV-1 quiescently infected PC12 cells (QIF-PC12), that were free of detectable infectious virus, were subjected to RPMI media containing BSA and NGF supplemented with 50 mM forskolin (Sigma) for 2 days at the indicated times. Forskolin was prepared in DMSO (Sigma) as recommended by Huang et al (1982).

Example 5
RNA Isolation and cDNA Synthesis

Cells were harvested for RNA isolation from duplicate wells on the days indicated by scraping cell sheets in PBS followed by centrifugation at 2,000 rpm for 5 min. Cell pellets were washed with PBS, pelleted as above and stored at −85° C. following removal of PBS. RNA was isolated using the Qiagen RNeasy Total RNA Kit as recommended by the manufacturer. 3 mg of each RNA sample was treated with DNAse I (Boehringer Mannheim, Indianapolis, Ind.) in 20 mM Tris-HCl (pH 8.4), 2 mMMgCl$_2$, 50 mM KCl, and 10 Units of RNase-free DNase I in a final volume of 20 ml at room temperature for 15 minutes. DNase I was inactivated by adding 2 ml EDTA (25 mM, pH 8.0) and heating at 65° C. for 10 min. cDNA was generated with SuperScript II reverse transcriptase (Gibco BRL) and random primers (Gibco BRL) as recommended by the supplier. cDNA was stored at −20° C. until use.

Example 6
RT-PCR

PCR reactions containing 20 mM Tris-HCl (pH 8.4), 50 mM KCl, 1.5mM MgC12, 0.2 mM each dNTP, 0.5 mM of each primer, 2.5 units Taq DNA polymerase (Gibco BRL) and cDNA derived from 1,500 cells were prepared on ice. Samples were denatured at 94° C. for 3 minutes followed by 35 cycles (94° C. for 45 seconds, 55° C. for 30 seconds, 72° C. for 90 seconds), for HSV target sequences, and 26 cycles, for the host target. Controls containing 10-fold dilutions of HSV-1 DNA ranging from 1.25 fg to 12.5 pg (7.5 to 75,000 genome equivalents) or 2-fold dilutions of PC12 cellular DNA ranging from 0.5 ng to 4.0 ng (155 to 1240 haploid genome equivalents) were performed in parallel to assess the levels of cDNA in each sample. Experimental and control samples were performed in duplicate and triplicate, respectively. The specificity of viral specific PCR products were verified by Southern blot analysis as described by Brown (1993). In brief, equivalent amounts of PCR products were applied to 2.0% agarose gels and electrophoresed in 0.5× TBE at 50V for 45–60 min. DNA was transferred to Magna NT nylon membranes (Micron Separation Inc., Westboro, Mass.) by capillary action following denaturation and neutralization. Membranes were hybridized to digoxigenin-labeled (DIG Oligonucleotides 3' end labeling and DIG Luminescent Detection Kits [Boehringer Mannheim]) probes specificfor HSV-1 gene sequences. The blots were scanned using the Phosphorimager (Molecular Dynamics, Sunnyvale, Calif.) and analyzed with GPTools software (Biophotonics, Ann Arbor, Mich.). Levels of the host glyceraldehyde-3-phosphate dehydrogenase (G3PDH) message were determined for each sample to monitor the reverse transcriptase reaction.

Example 7
Conditions for Maintenance of Long Term, Non-dividing Differentiated PC12 Cultures Previous studies have demonstrated NGF-differentiated PC12 (Nd-PC12) cells can be maintained as non-dividing cultures both in the presence and absence of serum (Greene, 1978; Greene and Tischler, 1976).These cultures have been studied on non-coated (Block et al, 1994) and collagen coated dishes (Greene and Tischler, 1976). Preliminary studies in our laboratory, however, indicated that a significant portion of PC12 cells cultured in the presence of serum continued to divide and is consistent with the findings of others (Goodman et al, 1979; Ignatius et al, 1985). Because a differentiated, non-dividing and adherent cell population was desired, we first determined whether continued growth of cells was the result of high plating density that may have exhausted the NGF supplied (Gunning et al, 1981). To make this determination, cells were plated at two different densities on collagen and non-collagen coated dishes. Cells plated at low density were NGF differentiated in the presence of serum (+serum) whereas those plated at high density were differentiated in the absence of serum (−serum). In collagen coated wells containing media supplemented with serum, the cell density increased more than 30-fold (i.e., from 5.5×103 to 1.9×10$^5$ cells/well) by 17 days post-plating(p.p.) with an additional 12-fold increase (to 2.4×10$^6$ cells/well) in the following 32 days. The cell density of parallel cultures grown on non-coated plates also continued to divide maintaining cell densities of about 50% of those cultured on collagen-coated dishes. When Nd-PC12 cells were grown on coated dishes in the absence of serum (−serum) a relatively constant cell number was maintained for 7 weeks with a subsequent loss of about 50% of the cells during the following 18 days. Parallel cultures maintained in serum free conditions did not adhere well to non-coated dishes. The addition of serum to minus-serum Nd-PC12 cultures on day 25 p.p. resulted in a 70% increase in cell number within 6 days and an additional 14-fold increase in the following 18 days achieving equivalent cell densities as +serum cultures. These data demonstrate that a relatively constant number of Nd-PC12 cells could be maintained as non-dividing cultures only when cultured in the absence of serum and that cell growth arrest is reversible upon the addition of serum to the media for up to 25 days p.p.

Figure 3:
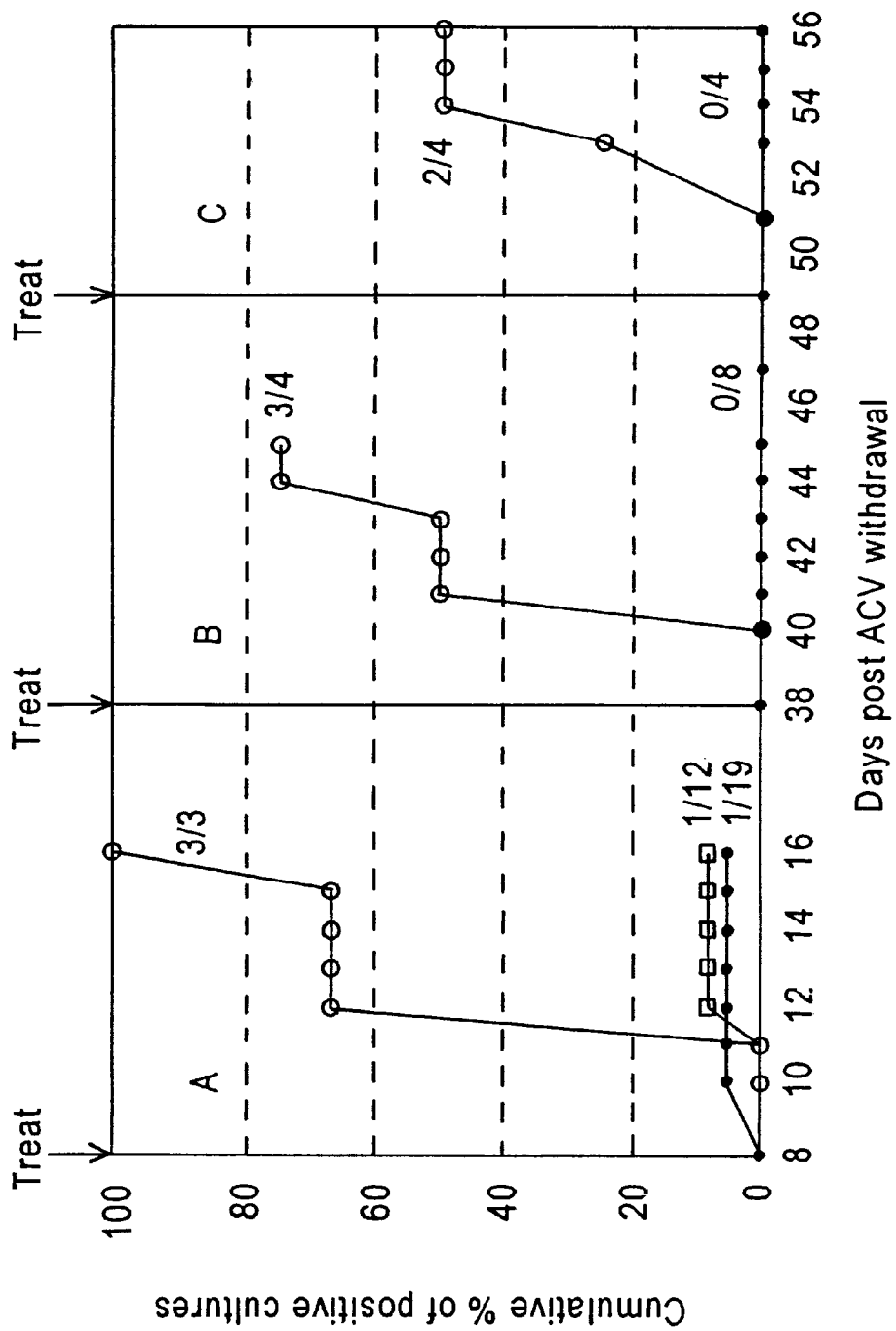
FIG. 3 shows induction of HSV-1 from long term quiescently-infected PC12 cells.

Example 8
Reactivation from Long-term (50 Days) HSV-1 Infected, Quiescent PC12 Cultures with Forskolin To determine whether Nd-PC12 cells could harbor HSV-1 in a recoverable state for long periods of time following removal of ACV, Nd-PC12 cultures were infected with strain KOS (M) at a MOI of 27+3 on day 15 p.p. and maintained as quiescently infected cultures (QIF-PC12) as described in FIG. 3. Under these conditions, all cultures were free of detectable levels of infectious virus in the supernatants at the time of ACV withdrawal. Virus was detected in only 1 of 35 cultures during the following 8 days, and virus was not detected from total cell lysates of our infected control wells on day 16 post-ACV withdrawal. To determine if NGF withdrawal would induce virus production, as described by Wilcox and Johnson (1987), NGF was withdrawn on day 8 post-ACV withdrawal. Virus was detected by day 8 post-treatment in 100% of forskolin-induced control cultures, 8% NGF-free cultures, and 5% of infected untreated control cultures. Except for the detection of virus in 2 of the remaining 14 infected untreated control wells on day 17 post-ACV withdrawal, virus was not detected in infected control wells for the remaining 39 days.

To determine whether these virus negative (non-producing) cultures were still capable of producing virus, 4 of 12 cultures were treated with forskolin on day 38, and 4 of 8 were treated with forskolin on day 49 post-ACV withdrawal. Induction with forskolin at these later dates resulted in the detection of virus in 75% and 50% of cultures, respectively, compared with 0% in the remaining infected untreated control cultures. These data indicate that virus can be recovered from long-term QIF-PC12 cultures when induced with forskolin.

Example 9

Figure 4:
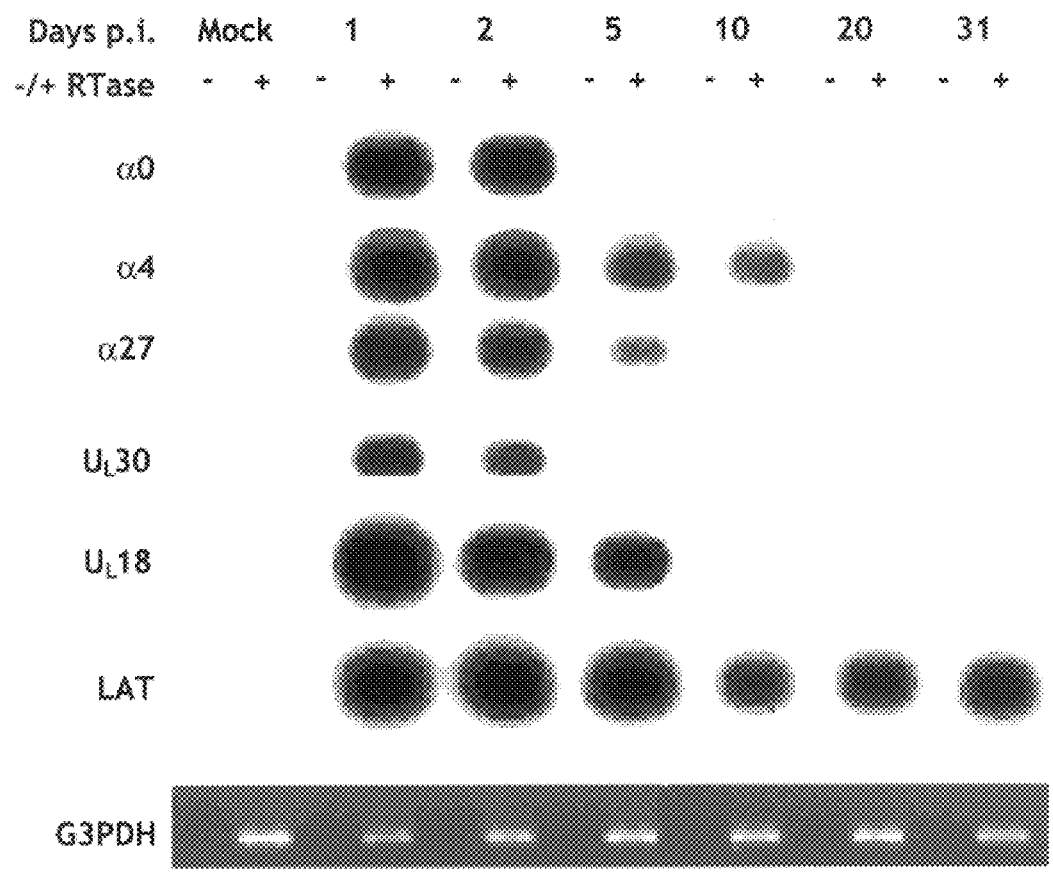
FIG. 4 shows Southern analysis of HSV-1 transcripts produced during the establishment and maintenance of the quiescent phase of infection.

Detection of Viral Transcripts During the Establishment and Maintenance of the Quiescent Phase of QIF-PC12 Cultures To study viral gene expression during the establishment and maintenance phases of a quiescent infection, QIF-PC12 cells were established under conditions that minimize the effects of high copy number of viral genomes. This was achieved using strain 17 because it reactivates more efficiently in this model than KOS. The infections were performed at an MOI of 0.5. The rate of virus reactivation from QIF-PC12 cells established under these conditions are presented in a subsequent manuscript (Danaher et al, 1999 J Neuro Virol). RNAs from duplicate QIF-PC12 cell cultures were collected at the indicated time points throughout the 31 day period and analyzed by RT-PCR in duplicate. The specificity of the RT-PCR products were confirmed by Southern blot analysis. FIG. 4 shows representative results from one of 4 samples from each time point examining the viral and host genes (G3PDH gene). A precipitous decline in transcripts occurred from the selected representatives of the 3 classes of the herpes virus genes (i.e., immediate-early [$\alpha$], early [$\beta$], late [$\gamma$]) tested following day 1 p.i. Detection of transcripts from a genes extended to as long as 10 days after drug removal (i.e., 20 days p.i.), as typified by the $\alpha$27 product. Transcripts from the UL30 (DNA polymerase gene), representing the $\beta$ genes, became undetectable by the day of ACV withdrawal (i.e., day 10 p.i.). Gamma genes, as represented by UL18 (VP23), were at, or below the level of detection by day 20 p.i. In contrast to the precipitous decline in all classes of viral gene transcripts represented, the stable LAT transcript persisted, although somewhat reduced compared to day 1 p.i. levels, for the length of the assay.

From FIG. 4, it is apparent that the products of the representative viral genes, except for LAT, diminished significantly throughout the 31 day period assayed. Expression of the host cell gene G3PDH was constant throughout the time period measured. Table 2 shows the values obtained from duplicate Southern analysis from duplicate cultures at each time point of viral RT-PCR products quantified by densitometry during the 31-day period. The sensitivity in all cases was greater than 0.1 target sequences per cell, with a range of 0.010 to 0.078 represented by VP23 and $\alpha$4, respectively. Consistent with the results shown in FIG. 4, a precipitous decline in viral transcripts associated with productive infection was determined following day 1 p.i., whereas levels of LAT remained relatively constant. Transcript production from the $\alpha$0 and UL30 (DNA polymerase gene) declined the fastest during the first five days p.i. By day 10 p.i. (day of ACV withdrawal), the level of UL18 (VP23) and a gene expression was down 93–99%, and the level of UL30 expression fell below the level of detection. Following the withdrawal of ACV, the expression of these genes continued to decline and by day 20 the average cDNA copies for the $\alpha$ genes were below the level of detection. By day 20 and thereafter, the average cDNA copies for UL18 were at the level of detection and below. In contrast, LAT transcripts were reduced 53% by day 10 p.i. but remained relatively constant thereafter, and never dropped near, or below, the level of detection in the assay. Host G3PDH RNA levels remained relatively constant throughout the assay period.

Example 10

Figure 2:
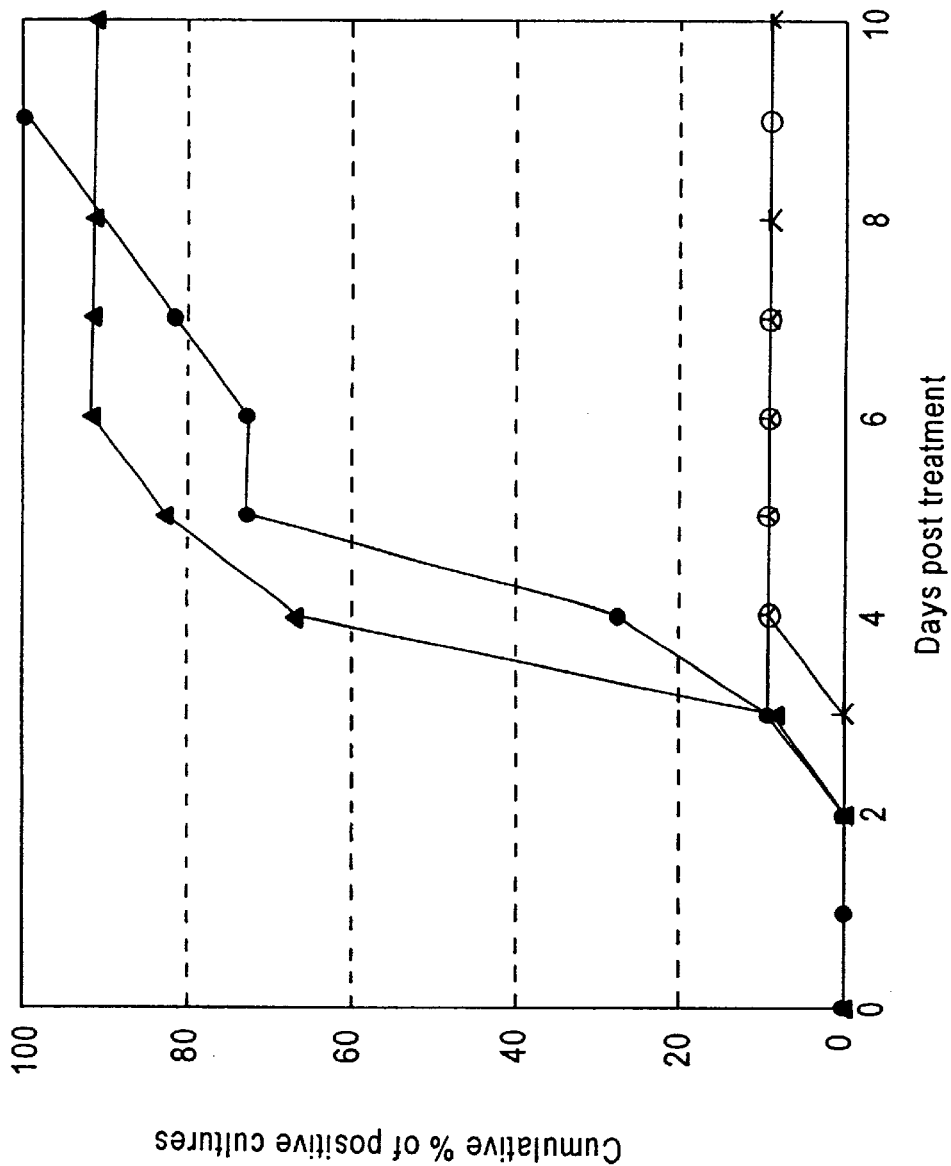
FIG. 2 shows induced HSV-1 production from quiescent-infected PC12 cell cultures.

Viral Specific Product was not Detected in Uninfected Control Cultures or in Minus Reverse-transcriptase Controls To strengthen the belief that the above analysis was undertaken on cells that were truly quiescent for HSV-1 genomes, parallel 12-well cultures,that were determined to be non-productive, were treated with forskolin on day 20 p.i. and reactivated with similar kinetics to that of KOS, as reported in the previous section, with 75% reactivation by 7 day post-forskolin treatment. This experiment was done under similar conditions described in FIG. 2.

Example 11

Asynchronous and Spontaneous Release of HSV-1 from PC-12 Cells

The lack of an adequate cell culture model for latency of herpes simplex virus type 1 (HSV-1) contributes to our poor understanding of HSV-1 reactivation. The objective of this research was to establish a latent cell culture model that supports HSV-1 in a state suitable for reactivation studies. Rat pheochromocytoma (PC-12) cells were grown in media containing 50 ng/mL nerve growth factor. Thirty-six individual cultures in 12-well plates were infected with HSV-1 (strain KOS) at a MOI of 20 in the presence of 50 mM acycloguanosine (ACY). After 10 days, ACY was removed (Day 0) and the level of virus replication was determined by direct plaque assay (DPA) on monolayers of monkey kidney (Vero) cells for up to 60 days. Results of the DPA showed that virus was spontaneously and asynchronously released from four different culture wells on days 8, 10, 17 and 32. Overall, the rate of virus shedding was 6 of 445 assays (1.3%). In comparison with ACY treated cultures, 100% of untreated cultures produced virus continuously until total cytopathic effect was achieved (mean 22 days) (p<0.001; Chi square). These data demonstrate that the majority of cells do not release virus, and the low rate of viral shedding from PC-12 cells is similar to the low rate of shedding that occurs in humans (Kameyama et al.,1988). This work provides preliminary evidence that HSV-1 can be harbored in a potentially latent state in cell culture, and that these cells may serve as a good model for studies of HSV-1 reactivation.

Example 12

HSV-1 Release from PC-12 Cells Induced by Heat Stress

Rat pheochromocytoma PC-12 cells were grown under conditions that result in non-dividing neuronally differentiated cells, infected with HSV-1 (17+) at a MOI of <1.0, and maintained in acyclovir (ACV) for 10 days as described. Eight days after ACV removal, cells were subjected to heat (39° C. to 43° C.) for 1 to 3 hrs, or 50 μm forskolin (positive control). The presence of virus on day 0–25 post-infection was determined using supernatants from infected cultures in a direct plaque assay (dpa).

| Treatment (Tx) | Positive Cultures post-Tx | Positive Cultures 5d post-Tx | Positive Cultures 7d post-Tx |
| --- | --- | --- | --- |
| 39° C. | 0/12 (0%) | 0/12 (0%) | 0/12 (0%) |
| 41° C. | 1/12 (8%) | 1/12 (8%) | 1/12 (8%) |
| 43° C. | 12/12 (100%) | 12/12 (100%) | 12/12 (100%) |
| Forskolin | 0/12 (0%) | 11/12 (92%) | 12/12 (100%) |
| DMSO | 0/12 (0%) | 0/12 (0%) | 0/12 (0%) |
| Negative control | 0/24 (0%) | 0/24 (0%) | 0/24 (0%) |

Virus was released more efficiently from cells subjected to 43° C. and forskolin compared with cells subjected to lower temperatures, whereas no virus was released from cells exposed to fresh media +/− DMSO ($p<0.001$; ANOVA). Consistent with our previous work, forskolin induced replication by day 5, however heat stress induced replication in 100% of cultures by day 2. These data show that virus replication can be efficiently, predictably and rapidly induced from a state of nonproductivity by heat shock, and that this system may serve as a cell culture model for the study of HSV-1 latency and reactivation.

Example 13
Effect of Hormones on HSV-1 Release from Nonpermissive PC-12 Cells

This study was conducted to identify biochemicals that could predictably release virus from this neuronal cell model. Individual PC-12 cultures grown, neuronally differentiated in 12-well plates, infected with HSV-1 (strain 17+) at a MOI of <1.0 and maintained in acyclovir (ACV) for 10 days. Eight days after ACV removal, cells were subjected to dexamethasone (20, 5, 1, 0.2 μM), epinephrine (100, 50, 10, 1 μM), estrogen (10, 2, 0.5, 0.1 nM), forskolin (50 μM) or control media. Supernatants from cultures were removed daily beginning day 10 post infection and the presence of virus was determined by direct plaque assay (dpa) for 18 days post-treatment (pTx). An average of <25 plaques per positive culture was rated light, an average of 26 to 75 plaques perpositive culture was rated moderate, and an average of >75 plaques per positive culture was rated heavy. Results showed that forskolin and estrogen caused significantly more virus replication than the other treatments ($p<0.05$, Chi square). Virus replication occurred in 8.0% of control cultures (days 2–16 pTx), 10.5% of dexamethasone-treated cultures (days 3–7 pTx), 15.3% of epinephrine-treated cultures (days 4–7 pTx), 28.6% of estrogen-treated cultures (days 5–18 pTx) and 74.3% of forskolin-treated cultures (days 4–7 pTx). The magnitude of viral release was heavy in cultures treated with forskolin and epinephrine, moderate with estrogen, and light with dexamethasone. Optimum viral shedding occurred when cells were treated with forskolin (50 μm), estrogen (2 nm), epinephrine (10 μm) and dexamethasone (1 μm). These data demonstrate that estrogen and forskolin trigger virus replication from non-permissive PC12 cells that harbor HSV-1, and that these agents may be useful for study of events that regulate HSV reactivation.

Example 14
Strain Specificity for HSV-1 Replication in PC12 Cells

The aim of this study was to determine whether our cell culture model for HSV-1 latency displayed strain specificity. Rat pheochromocytoma PC12 cells were grown under conditions that result in non-dividing neuronally differentiated cells. Cells were infected with HSV-1 (strains KOS, 17+, McKrae, and 2903 [a McKrae LAT-deficient mutant]) at MOIs 0.5 to 20, and maintained in acycloguanosine (ACV) for 8 days as described. Virus replication was detected using supernatants from infected cultures in a direct plaque assay (dpa) using monkey kidney (Vero) cells. During the week following ACV removal, HSV-1 was detected in 88 and 96% of cultures infected with McKrae (MOI=4 and 20, respectively), 38 and 71% of cultures infected with 17+ (MOI=0.5 and 2.5, respectively), 4 and 12% of cultures infected with KOS (MOI=1 and 5.6, respectively), and 0% of cultures infected with 2903 (MOI=2 and 10). These data indicated that two of the strains (KOS, 2903) were suitable for reactivation studies. To induce replication in non-productive cells, KOS-and 2903-infected cultures were subjected to forskolin (50 mm) 20 days post infection.

| Strain | MOI | Positive Cultures 7d After Mock-Treatment | Positive Cultures 7d After Forskolin-Treatment |
| --- | --- | --- | --- |
| KOS | 1.1 | 0/11 (0%) | 7/12 (58%) |
| KOS | 5.6 | 1/12 (8%) | 7/9 (78%) |
| 2903 | 2 | 0/12 (0%) | 2/12 (17%) |
| 2903 | 10 | 0/12 (0%) | 2/12 (17%) |

Data in the table shows that a significantly greater percentage of cultures produced virus when subjected to forskolin compared with mock-treated cultures ($p<0.01$, Chi square), and a relationship between MOI and inducible replication in KOS-infected cultures existed. These data suggest that there is strain specificity for establishment of a "latent state" and for inducible-replication in PC12 cells, and that a high viral-to-cell inoculum ratio may provide a viral advantage for entering latency. Also, the deletion of LAT sequences may inhibit the virus' ability to replicate in neuronally differentiated PC12 cells.

Example 15
Serotype Specificity for HSV Replication in PC12 Cells

The aim of this study was to determine whether HSV replication displayed serotype specificity in neurally-differentiated, rat pheochromocytoma PC12 cells. Cells were grown under conditions that result in non-dividing neuronally differentiated cells as described, and infected with HSV-1 or HSV-2 at MOI<1.0 in the presence (HSV-1 strain 17+; HSV-2 strains 333, G) or absence of ACV (HSV-1 strains 17+, McKrae, KOS, 2903, 2903r). Antiviral therapy was continued for 8 days. Virus replication was detected using supernatants from infected cultures in a direct plaque assay (dpa) using monkey kidney (Vero) cells. In the absence of ACV, all HSV-1 strains replicated in PC12 cells, however HSV-2 (G) did not grow. In the presence of ACV, a nonproductive state was established. In an attempt to induce replication in non-productive cells, cultures were subjected to forskolin (50 mM) or heat stress (43° C., 3 hrs) 19 days and 26 days post infection [pi], respectively. HSV-1 (17+) was shed from 12/12 cultures 4 days after forskolin treatment and 32/33 cultures 2 days after heat stress compared with 2/22 control cultures ($p<0.01$, Chi square). HSV-2 (333) was minimally shed from 4/46 cultures 2 days after heat stress, 1/24 cultures after forskolin treatment and 0/23 control cultures. HSV-2 (G) was shed from 1/24 cultures 2 days after heat stress, 0/12 cultures after forskolin treatment and 0/12 control cultures. These data suggest that there is serotype specificity for HSV replication, and inducible-replication, in PC12 cells, and that ACV affects this susceptibility.

We claim:

1. A PC12 cell quiescently infected with a human herpes simplex 1 virus.

2. A method of reactivating a quiescent virus from at least one quiescently-infected PC12 cell, comprising: introducing a reactivator to a cell of claim 1.

3. A method for determining the ability of a test reagent to suppress virus reactivation from a quiescently-infected PC12 cell of claim 1, comprising:

introducing a test reagent to said PC12 cell; and introducing to said PC12 cell a reactivator; and determining if reactivation has been suppressed.

4. A method for determining the ability of a test reagent to induce virus reactivation from a PC12 cell of claim 1, comprising:

introducing a test reagent to said PC12 cell; and determining if reactivation has been induced.

5. A method for eliciting phenotypic change in a PC12 cell of claim 1, introducing a reactivator to said PC12 cell, and eliciting a phenotypic change in said PC12 cell.

6. The method of claim 5 wherein said phenotypic change is selected from the group consisting of synthesis of myelin, synthesis of neurotransmitter, cell death, and viral shedding.

7. A method for determining the susceptibility of a person infected with a quiescent virus to reactivation by a reagent, comprising:

introducing a reactivator to a PC12 cell of claim 1, wherein the neurotropic virus is a strain isolated from a person infected with said neurotropic virus; and determining the relative magnitude of phenotypic or genomic reactivation.

8. A method to identify nucleic acid molecules and/or proteins involved in virus reactivation, comprising:

reactivating a PC12 cell of claim 1 with a reactivator; and identifying nucleic acid molecules and/or proteins which are uniquely expressed during reactivation.

9. A method to identify the origins of DNA replication important to virus reactivation, comprising:

reactivating a PC12 cell of claim 1 with a reactivator; and identifying the origins of replication which are uniquely associated with reactivation.

10. A method to screen an altered virus' relative ability to be reactivated, comprising:

introducing a reactivator to a PC12 cell of claim 1, wherein the neurotropic virus is an attenuated neurotropic virus; and determining the relative magnitude of reactivation.

11. A method of establishing quiescently-infected PC12 cells, comprising:

introducing a human herpes simplex 1 virus to neurally-differentiated and viable PC12 cells in a serum-free medium, said differentiated PC12 cells being in a container; and incubating said container with an antiviral reagent for a time necessary to accomplish quiescence of viral activity; and removing said antiviral agent from said container.

12. The method of claim 11, wherein the antiviral reagent is acyclovir.

13. The method of claim 12, wherein said container is incubated with acyclovir for approximately 5 to 12 days.

14. The method of claim 13, wherein said container is incubated at a temperature less than 40 degrees Celsius.

15. The method of claim 12, wherein said serum free medium allows for constant cell density and imparts neural characteristics to said cells.

16. A method to determine the ability of a non-neurotropic virus to become quiescent and/or reactivatable in a PC12 cell line, comprising:

introducing a non-neurotropic virus to differentiated and viable PC12 cells in a serum-free medium, said differentiated PC12 cells being in a container; and incubating said container with an antiviral reagent for a time necessary to accomplish quiescence of viral activity; and removing said antiviral agent from said container; and determining said non-neurotropic virus' ability to become quiescent and/or reactivatable.

17. A method to determine a reagent's ability to inhibit establishment of a quiescent viral infection, comprising:

introducing a virus to differentiated and viable PC12 cells in a serum-free, test reagent-containing medium, said differentiated PC12 cells being in a container; and incubating said container with an antiviral reagent for a time necessary to accomplish quiescence of viral activity in the absence of said test reagent; and removing said antiviral agent from said container; and determining said test reagent's ability to inhibit quiescence.

* * * * *